United States Patent [19]
Kinney et al.

[11] Patent Number: 5,909,276
[45] Date of Patent: Jun. 1, 1999

[54] OPTICAL INSPECTION MODULE AND METHOD FOR DETECTING PARTICLES AND DEFECTS ON SUBSTRATES IN INTEGRATED PROCESS TOOLS

[75] Inventors: Patrick D. Kinney, Santa Clara, Calif.; Nagaraja P. Rao, Minneapolis, Minn.

[73] Assignee: MicroTherm, LLC, Minneapolis, Minn.

[21] Appl. No.: 09/050,267

[22] Filed: Mar. 30, 1998

Related U.S. Application Data

[60] Provisional application No. 60/042,202, Mar. 31, 1997.

[51] Int. Cl.$^6$ .................................................. G01N 21/00
[52] U.S. Cl. .................... 356/237; 356/430; 356/336; 356/337; 356/342
[58] Field of Search ................... 356/237, 430, 356/335, 336, 337, 338, 342

[56] References Cited

U.S. PATENT DOCUMENTS

| | | | |
|---|---|---|---|
| 3,790,287 | 2/1974 | Cuthbert et al. | 356/120 |
| 4,342,515 | 8/1982 | Akiba et al. | 356/237 |
| 4,377,340 | 3/1983 | Green et al. | 356/237 |
| 4,378,159 | 3/1983 | Galbraith | 356/237 |
| 4,569,695 | 2/1986 | Yamashita et al. | 134/1 |
| 4,655,592 | 4/1987 | Allemand | 356/237 |
| 4,692,223 | 9/1987 | Lampert et al. | 204/34.5 |
| 4,772,126 | 9/1988 | Allemand et al. | 356/336 |
| 4,895,446 | 1/1990 | Maldari et al. | 356/336 |
| 5,189,481 | 2/1993 | Jann et al. | 356/73 |
| 5,274,434 | 12/1993 | Morioka et al. | 356/237 |
| 5,317,380 | 5/1994 | Allemand | 356/338 |
| 5,417,537 | 5/1995 | Miller | 414/217 |
| 5,450,205 | 9/1995 | Swain et al. | 356/382 |
| 5,479,252 | 12/1995 | Worster et al. | 356/237 |
| 5,493,123 | 2/1996 | Knollenberg et al. | 250/372 |
| 5,631,733 | 5/1997 | Henley | 356/327 |

OTHER PUBLICATIONS

W.P. Shaw and R.P. Sopher, "High Speed Automatic Particle Counter", IBM Technical Disclosure Bulletin, vol. 17, No. 9, Feb. 1975.

D.R. Oswald and D. F. Munro, "A Laser Scan Technique for Electronic Materials Surface Evaluation", *Journal of Electronic Materials*, vol. 3, No. 1, 1974.

*Primary Examiner*—Robert Kim
*Assistant Examiner*—Reginald A. Ratliff
*Attorney, Agent, or Firm*—Westman, Champlin & Kelly, P.A.

[57] ABSTRACT

An optical inspection module detects defects on an active surface of a substrate in an integrated process tool system. The optical inspection module includes an enclosure, a substrate holder, a light source, a light beam path, a lens and a photodetector array. The light source has a light beam port. The light beam path extends from the light beam port to the substrate holder and has a grazing angle of incidence with respect to the active surface of the substrate. The light beam path illuminates substantially the entire active surface. The lens is oriented to collect non-secularly reflected light scattered from the light beam path by any defects on the active surface. The photodetector array has a plurality of pixels which are positioned within a focal plane of the lens. Each pixel corresponds to an area on the active surface, and the plurality of pixels together form a field of view that covers substantially the entire active surface.

40 Claims, 7 Drawing Sheets

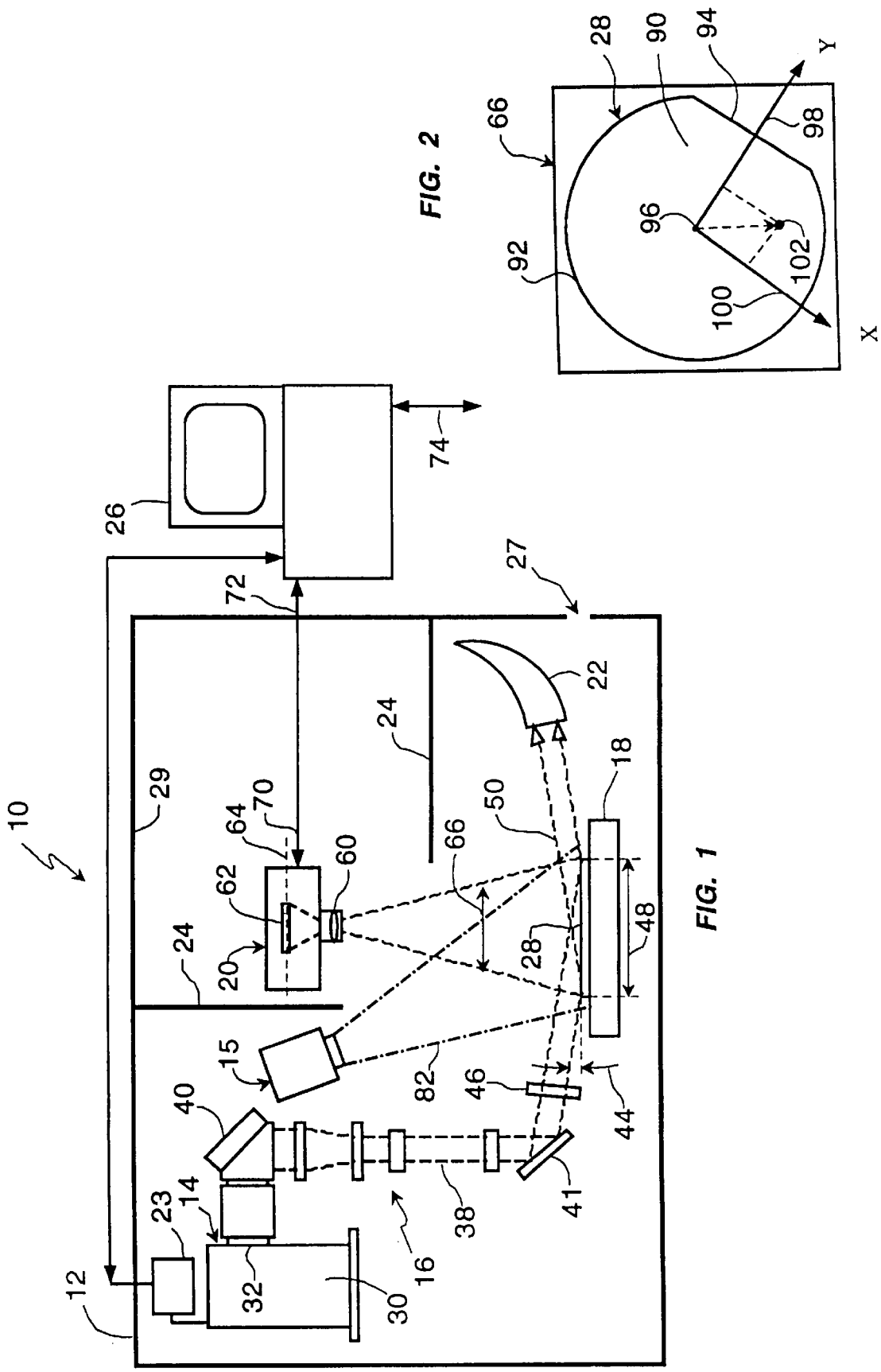

OPTICAL INSPECTION MODULE AND METHOD FOR DETECTING PARTICLES AND DEFECTS ON SUBSTRATES IN INTEGRATED PROCESS TOOLS

CROSS-REFERENCE TO RELATED APPLICATION

This application claims the benefit of U.S. provisional application Ser. No. 60/042,202, filed Mar. 31, 1997 and entitled "LARGE-AREA DARKFIELD INSPECTION SYSTEM (LADIS) FOR DETECTION OF PARTICLES ON SEMICONDUCTOR WAFERS AND OTHER SUBSTRATES IN INTEGRATED PROCESSING ENVIRONMENTS."

BACKGROUND OF THE INVENTION

The present invention relates to an optical inspection apparatus for detecting particles and surface defects on electronic or magnetic substrates. More particularly, the present invention relates to an apparatus for imaging the entire substrate within an integrated processing environment.

The presence of contaminant particles on the surface of electronic substrates such as semiconductor wafers can lead to the formation of defects during the microelectronics fabrication process. In order to maintain high manufacturing yield and thus low manufacturing costs, it is necessary that contaminated wafers be identified and cleaned during the manufacturing process.

In general, wafer inspection systems have been configured as highly sensitive, stand-alone inspection systems which typically have dedicated material handling systems for handling the substrates to be inspected. These systems are designed to provide sensitivity to extremely small defects and particles. This is generally accomplished by minimizing the background scattering from the surface either by using a small laser spot size (in laser scanning systems) or a high magnification objective lens for camera based inspection systems. In addition, many of these inspection systems use special techniques to minimize background scatter when inspecting patterned substrates, such semiconductor wafers formed by photolithography etching and deposition process steps. These systems are thus complex in design and expensive. The high cost of these inspection systems necessarily means that the number of such systems present in production lines is low. As a result, inspections for particles and defects are relatively few and far between. Since a very large number of process steps are involved in the processing of electronic substrates, the low frequency of wafer inspections between process steps may lead to contaminated substrates remaining undetected for a long period of time. This leads to lower yield and increased rework costs.

The present invention addresses these and other problems, and offers other advantages over the prior art.

SUMMARY OF THE INVENTION

The optical, substrate inspection module of the present invention detects defects on an active surface of a substrate in an integrated process tool system. The inspection module includes an enclosure, a substrate holder, a light source, a light beam path, a lens and a photodetector array. The light source has a light beam port. The light beam path extends from the light beam port to the substrate holder and has a grazing angle of incidence with respect to the active surface of the substrate. The light beam path illuminates substantially the entire active surface. The lens is oriented to collect non-secularly reflected light scattered from the light beam path by any defects on the active surface. The photodetector array has a plurality of pixels which are positioned within a focal plane of the lens. Each pixel corresponds to an area on the active surface, and the plurality of pixels together form a field of view that covers substantially the entire active surface.

In one aspect of the present invention, the inspection module is incorporated in an integrated cluster tool processing system. The system includes a loading module having a substrate loading input, a plurality of substrate processing modules, and the optical inspection module. A common substrate transport arm interfaces with the substrate loading input, each of the substrate processing modules and the inspection module along a substrate travel path.

In another aspect of the present invention, the inspection module is incorporated in a substrate polishing and inspection apparatus. The apparatus includes a substrate travel path for carrying the substrate to be polished, a polishing station which is positioned along the substrate travel path, a cleaning station which is positioned along the substrate travel path downstream of the polishing station, a drying station which is positioned along the substrate travel path downstream of the cleaning station and the substrate inspection station which is positioned along the substrate travel path downstream of the drying station.

Yet another aspect of the present invention relates to a method of polishing and inspecting the substrate. Yet another aspect of the present invention relates to a semiconductor wafer processing and inspection chamber for processing and in-situ inspecting an active surface of a semiconductor wafer.

BRIEF DESCRIPTION OF THE DRAWINGS

FIG. 1 is a schematic representation of a large area optical inspection module according to one embodiment of the present invention.

FIG. 2 is a top plan view of a substrate image in the inspection module under brightfield illumination.

DETAILED DESCRIPTION OF THE PREFERRED EMBODIMENTS

Figure 3:
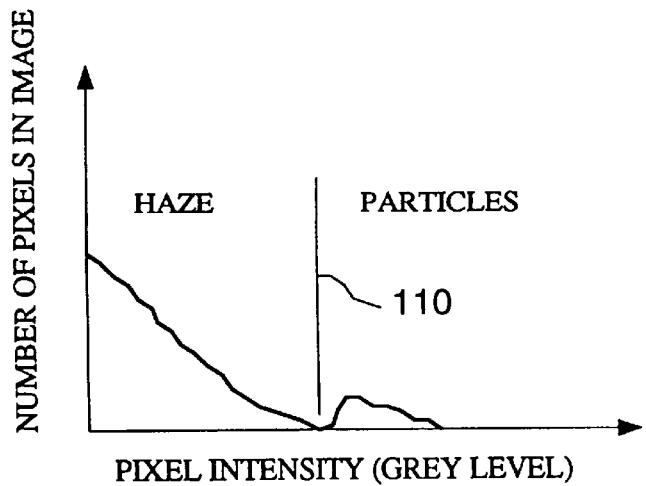
FIG. 3 is histogram illustrating an example of the number of pixels as a function of grey level value in an image of the substrate.

FIG. 1 is a schematic representation of a large area optical inspection module 10 for detecting particles and other defects on large substrates such as semiconductor wafers, flat panel displays, rigid magnetic recording disks and electronic packaging substrates, for example. Inspection module 10 includes enclosure 12, light sources 14 and 15, beam-conditioning unit 16, substrate holder 18, charge coupled device (CCD) array camera 20, light trap 22, partitions 24 and computer controller 26. Inspection module 10 further includes an entrance, gate or door 27 in enclosure 12 through which substrates, such as substrate 28, are loaded into and unloaded out of enclosure 12. Enclosure 12 is preferably light-proof and has light-absorbing internal surfaces 29 for minimizing deleterious effects of internal and external stray light during inspection. Partitions 24 also have light-absorbing surfaces to shield camera 20 from internally generated stray light. In one embodiment, enclosure 12 forms a vacuum chamber, and the components internal to enclosure 12 are vacuum-compatible components.

Light source 14 has a housing 30 and a light beam port 32. Light source 14 preferably includes a stationary, high incident power, broadband light source. For example, light source 14 can include a commercially available 75 W–300 W xenon arc lamp or a 50 W–250 W quartz tungsten halogen (QTH) lamp, which emits a collimated, 1 inch or larger diameter circular light beam of uniform intensity through light beam port 32. Lamp housing 30 can include a convection-cooled housing with two light beam ports 32 or an air-cooled housing with one light beam port 32. A convection-cooled housing can accommodate up to a 100 W light source, and an air-cooled housing can accommodate up to a 250 W light source, for example. A lower powered, 50 W light source is preferred because it has a much longer average life than higher powered light sources. Light source 14 uses an external power supply (not shown) that runs on 120 VAC and, at 50 W, draws roughly 1 ampere of current. In one embodiment, light source 14 includes a light intensity controller 23 which monitors and controls the light output. Light intensity controller 23 is coupled to computer controller 26 to assist computer controller 26 in detecting light failure and estimating defect sizes.

Beam-conditioning unit 16 includes optics for shaping the light beam emitted by light source 14 through light beam output 32, a conditioner for making the light beam more uniform, and mirrors such as mirrors 40 and 41 for defining a light beam path 38 from light beam port 32 to the active surface of substrate 28. In one embodiment, mirror 40 is a dichroic mirror which limits the spectral output of light source 14 to a wavelength range of 430–620 nm. A limited spectral output has the advantage of higher resolution imaging because of reduced chromatic aberration in beam-conditioning unit 16. The total power from light source 14 over this wavelength range is estimated to be 270 mW. A half-wave plate 46 is positioned within light beam path 38 to produce s-polarized light.

The light beam passing through light beam path 38 illuminates substantially the entire active surface of substrate 28. Light beam path 38 is oriented to form a grazing angle of incidence 44 relative to the active surface of substrate 28. A grazing angle of incidence is defined as an incidence angle between 80 degrees and 90 degrees from a vector normal to the active surface of substrate 28. In order to illuminate substrate 28 at a large incident angle without wasting power, beam-conditioning unit 16 transforms the circular light beam received from light beam port 32 to a quasi-rectangular beam. The circular-to-rectangular transformation can be accomplished with a series of cylindrical lens or a circular-to-rectangular fiber optic bundle with appropriate beam shaping optics on each end of the bundle.

Substrate 28 has a diameter 48. In one embodiment, inspection module 10 is configured for inspecting substrates having a diameter of 200 mm. In this embodiment, beam-conditioning unit 16 transforms the circular light beam to a quasi-rectangular beam having a length of just over 200 mm, allowing the entire surface of substrate 28 to be illuminated at one time.

In addition to broad band light sources, light source 14 can also include a monochromatic laser light source such as a high power laser line generator (e.g. a Lasers Model Magnum 670 nm, 500 mW laser source), or a commercially available laser parallel line generator source. With a laser light source, beam-conditioning unit 16 expands and shapes the resulting light beam so that the entire substrate 28 can be illuminated at a grazing angle.

As the light beam from light source 14 reflects off of the active surface of substrate 28, particles or other surface defects residing on the active surface scatter light from the light beam path. The scattered light from the active surface is referred to as non-specularly reflected light. The intensity of the scattered light due to a defect is a function of the size of the defect. Specularly reflected light 50 is trapped by light trap 22.

Camera 20 is supported above substrate 28 and is orientated to make imaging measurements of the non-specularly reflected light that is scattered from particles and other defects on the active surface of substrate 28. Camera 20 preferably has a variable exposure to enable the detection to be optimized with respect to particle size and surface conditions. Camera 20 preferably includes a scientific grade, slow-scan, cooled CCD camera, such as a commercially available Photometrics Model 300 series camera, which is operated in a high signal-to-noise mode for detection of weak signals on bright backgrounds. Cooled CCD cameras have an active cooling device, such as a thermoelectric cooling device, for cooling the photodetector array. Cooled CCD cameras have lower dark current. Slow-scan CCD cameras have image readout times that are much slower than video cameras, such as 0.1 frames per second to 10 frames per second, depending on the size of the photodetector array. Slow-scan CCD cameras also do not need to operate continuously, and inspection module can therefore acquire snapshot images on command. Slow-scan CCD cameras have low read-out noise. In an alternative embodiment, camera 20 includes a video camera. Conventional video cameras produce images at 30 frames/second, and operate in a continuous mode.

Camera 20 includes a lens 60 and a charge-coupled device photodetector array 62. Lens 60 collects a fraction of the light scattered from the active surface of substrate 28 and applies the collected, scattered light to photodetector array 62. Lens 60 can include a commercially available high resolution camera lens for providing adequate light collection for the selected spatial resolution, such as an "enlarging" lens with an aperture of F/2.8 and focal length of 50 mm. Lens 60 can include a Rodenstock Apo-Radagon-N series or Rodagon series lens, for example. Lenses with variable magnification ranges may be used to image differently sized substrates.

Photodetector array 62 is positioned within a focal plane 64 of lens 60. Photodetector array 62 is divided into a plurality of pixels, with each pixel corresponding to unit area on the active surface of substrate 28. The plurality of pixels together have a field of view 66 which covers substantially the entire active surface of substrate 28. A large photodetector array is desired for good spatial resolution.

In one embodiment, photodetector array 62 includes an array of 1024 by 1024 pixels, wherein each pixel has an area of 24 µm by 24 µm on photodetector array 62. If diameter 48 of substrate 28 is 200 mm, then diameter 28 will be spanned by a line of 1024 pixels in photodetector array 62. This results in a magnification of approximately 0.12 and an imaged pixel size on the active surface of substrate 28 of approximately 200 µm by 200 µm. Larger photodetector array formats, such as 2K by 2K arrays and 4K by 4K arrays, for example, can be used to obtain better resolution.

Camera 20 preferably includes digitizing and computer interfacing circuitry in which the light intensities detected within each pixel of photodetector array 62 are converted to form a grey level image. The grey level image is coded in a standard format, such as an 8-bit or 16-bit TIFF format, which is provided to output 70. Output 70 can include an 8-bit, 12-bit or 16-bit output, for example. A 12-bit output provides a high definition image with a 4096 grey level image depth. A 16-bit output provides a 65,536 grey level image depth.

Computer controller 26 preferably includes an Intel® Pentium® Microprocessor-based workstation having standard communications interfaces 72 and 74. Interface 72 is coupled to output 70 to enable computer controller 26 to communicate with camera 20. Interface 72 can includes an RS 232 or an IEEE 488 interface, for example. Interface 74 can include an SECS interface, for example, to enable computer controller 26 to communicate with other computers in a multi-process cluster tool system. The information communicated to the other computers can include inspection status, inspection data, analysis results, a pass/fail signal or test scheduling information for example.

Computer controller 26 is provided with software drivers for controlling the operation of camera 20, communicating with other computers and analyzing images acquired by camera 20. All software is stored in memory (not shown) which is associated with computer controller 26. During inspection, the images acquired by camera 20 are processed by computer controller 26 to identify and count particles and other defects such as scratches, stains, residue, finger prints and pits. The inspection may involve several camera exposure steps under different illumination conditions, such as (i) acquiring an image of substrate 28 under brightfield illumination for the purpose for determining the orientation of substrate 28 and (ii) acquiring one or more images of substrate 28 illuminated at a grazing angle for the purpose of obtaining high quality, low noise images of defects on the active surface of substrate 28.

Brightfield illumination is provided by auxiliary light source 15. Light source 15 generates a light beam 82 which is orientated substantially normal to the active surface of substrate 28 and illuminates substantially the entire active surface of substrate 28. Specularly reflected light from the surface of substrate 28 is collected by lens 60 and applied to photodetector array 62. The image acquired under brightfield illumination is analyzed by computer 26 to detect the perimeter of substrate 28 by using edge detection software.

FIG. 2 is a top plan view of an image of substrate 28 within field of view 66 of camera 20 under brightfield illumination by light source 15. Field of view 66 covers substantially the entire active surface 90 of substrate 28. In the embodiment shown in FIG. 2, substrate 28 includes a perimeter 92 having an orientating feature 94, such as a wafer flat (as shown) or a notch (not shown), for the edge detection software. The location of perimeter 92 and the location of orientating feature 94 may be used to determine the orientation of substrate 28 with respect to camera 20. This information can also be used to establish a coordinate frame of reference for defining the position of particles and other defects that are detected in subsequent inspection steps. For example, a Cartesian (X-Y) coordinate reference frame may be established which has an origin 96 at the center of the circular arc portion of perimeter 92, a Y-axis 98 that bisects orientating feature 94 and an X-axis 100 that is perpendicular to Y-axis 98. The position of a detected particle 102 can then be defined along Y-axis 98 and X-axis 100, relative to origin 96.

Once the orientation of substrate 28 has been established, camera 20 captures images of substrate 28 while illuminated by light source 14 at a grazing angle. These images are analyzed by computer controller 26 to determine the number and location of particles and other defects on active surface 90. The presence of particles and other defects within each unit area of substrate 28 is identified as a function of the measured intensity within the corresponding pixel in photodetector array 62. In one embodiment, the measured intensity, or grey level value, within each pixel is compared with an intensity threshold. This allows light scattering caused by particles to be distinguished from light scattering caused by surface roughness. Each pixel having a measured intensity that exceeds the intensity threshold corresponds to an area on substrate 28 having a particle or other defect. A list of particle or defect locations on substrate 28 is generated based on the location of each of these pixels relative to the other pixels in photodetector array 62. Multiple intensity threshold levels can also be used.

A count of the total number of particles residing on active surface 90 of substrate 28 is generated based on a count of the number of pixels having a measured intensity that exceeds the intensity threshold. In one embodiment, groups of these pixels that are spatially contiguous with one another in photodetector array 62 are considered as representing a single defect on active surface 90. The shape of the defect can be analyzed to classify the type or source of the defect, such as a particle, a stain, a finger print or a scratch.

FIG. 3 is histogram illustrating an example of the number of pixels as a function of grey level value in an image of substrate 28. Line 110 represents the intensity threshold. Pixels having a grey level value above intensity threshold 110 are activated by light scattered from particles above a predetermined size. Pixels having a grey level value below intensity threshold 110 are activated by light scattered from particles or surface roughness below the predetermined size.

Image enhancement techniques may be used to obtain the highest sensitivity to particles and defects. For example, multiple images of the same substrate may be averaged to reduce random noise. Also, contrast between light scattering due to particles and light scattering due to surface roughness or haze can be improved by applying background subtraction. In one embodiment, a surface roughness intensity value, which is representative of the surface roughness of substrate 28, is subtracted from the measured intensity at each pixel location before the measured intensities are compared with the intensity threshold.

In an alternative embodiment, computer controller 26 obtains background images of several clean, defect free substrates with camera 20 under similar lighting conditions. Computer controller 26 averages these background images, and stores the resulting image in memory. During inspection of a substrate such as substrate 28, the stored, averaged background image is retrieved from memory and subtracted from the acquired image of substrate 28.

Figure 4:
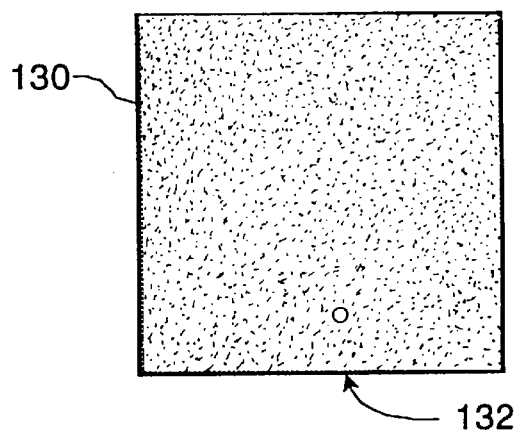
FIG. 4 is a diagram illustrating a substrate image illuminated at a grazing angle.
Figure 5:
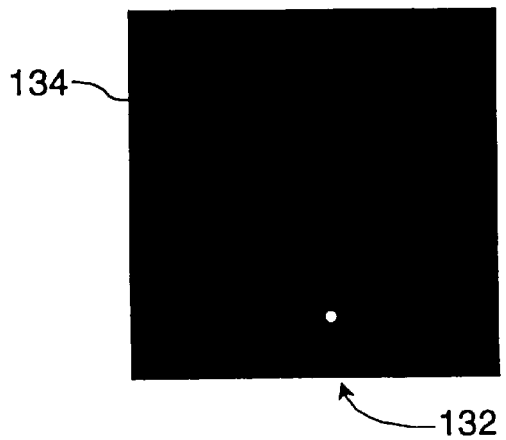
FIG. 5 is a diagram illustrating the substrate image of FIG. 4 after subtraction of a stored background image.

FIG. 4 is a diagram illustrating an image 130 of substrate 28 acquired by camera 20 while the substrate is illuminated at a grazing angle. A single particle 132 is represented by a bright spot on image 130. Contrast between the bright spot and the remainder of the image is somewhat low. FIG. 5 is a diagram illustrating an image 134 of substrate 28 after subtraction of the stored background image. The contrast between particle 132 and the remainder of the image is improved.

Since the intensity of light scattered by background surface roughness can be spatially non-uniform, computer controller 26 preferably performs the background subtraction step before applying intensity threshold 110. The background intensity can be spatially non-uniform due to non-uniform illumination intensity, non-uniform distribution of surface roughness or haze or a combination of both.

With patterned substrates, such as electronic semiconductor wafers, the background intensity distribution can vary to some extent with substrate type and orientation of the substrate with respect to the illumination. A range of substrate types and orientations can be acquired and stored in a background library by computer controller 26. During inspection, computer controller 26 can select corresponding t image corresponding to the type and orientation of the substrate being inspected from the background library and then subtract the selected background image from the acquired image. Alternatively, computer controller 26 can perform background subtraction using local area background estimates at a given pixel obtained by averaging the measured intensity values of neighboring pixels, which are determined to be substantially particle free.

In addition to defect detection software, computer controller 26 is preferably provided with software for performing signature analysis of the images acquired from the inspected substrates to detect "out-of-control" process conditions. In one embodiment, an out-of-control process condition is detected by comparing the image acquired from the substrate being inspected with images from a signature library which have previously been found to correlate with an out-of-control process condition.

Inspection module 10, as shown and described with reference to FIGS. 1–5, can be easily integrated as one of several processing module in a multi-process "cluster tool" system. A cluster tool is a manufacturing system that includes a set of environmentally isolated process chambers or modules which are linked by a common material handling interface and a common computer communications interface. The common material handling interface transports a workpiece between the various modules in the system. The common computer communications interface controls the sequential process steps. Clustering multiple operations within a single manufacturing system leads to benefits such as increased process yield (due to less wafer handling and improved process control) and reduced process cycle time. There are several types of clustering systems, such as vacuum cluster tools for deposition and etching, and lithography cluster tools. The inspection module of the present invention provides a simple, inexpensive and compact wafer inspection system that can be integrated into such a cluster tool system so that the elapsed time between processing and inspection can be minimized. For example, the inspection module of the present invention can be integrated with a substrate polishing or cleaning apparatus to form a cluster tool system for cleaning and inspecting substrates.

Figure 6:
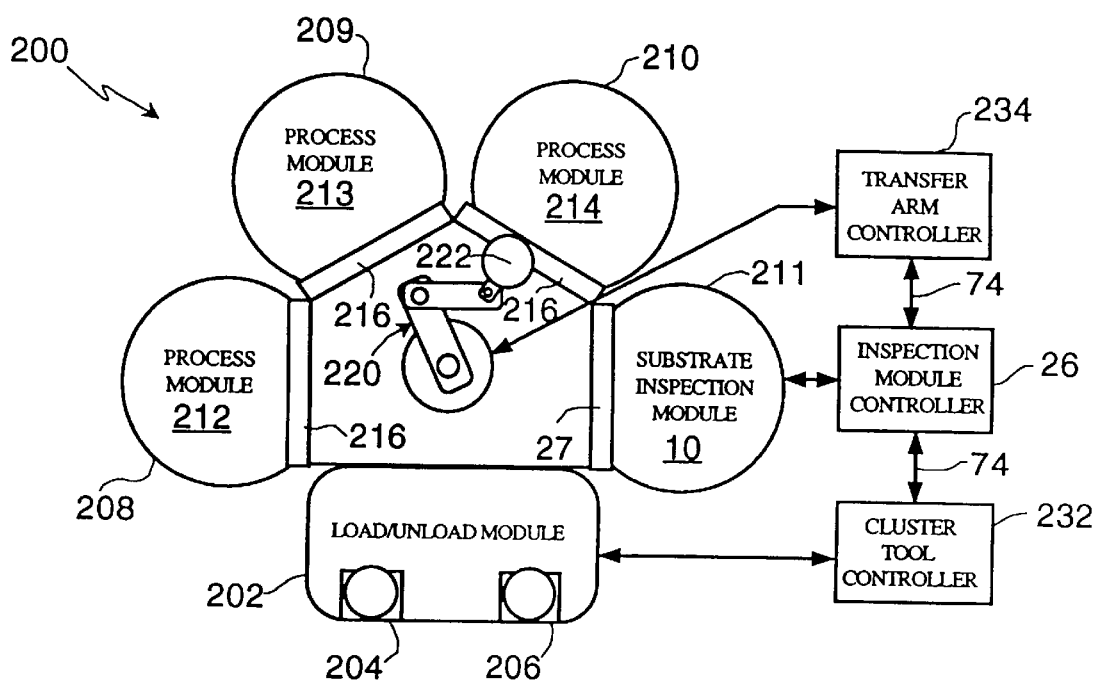
FIG. 6 is a schematic illustration of a multi-process cluster tool system in which the inspection module of the present invention has been integrated.

FIG. 6 is a schematic illustration of a multi-process cluster tool system in which the inspection module of the present invention has been integrated. Cluster tool system 200 includes a substrate loading/unloading module 202 having a loading input 204 and an unloading output 206. In one embodiment, loading input 204 and unloading output 206 include substrate carriers which hold a plurality of substrates to be loaded into or unloaded out of cluster tool system 200. Cluster tool system 200 further includes a plurality of substrate processing stations 208–211. Processing modules 212–214 are positioned at processing stations 208–210, respectively. Inspection module 10 is positioned at processing station 211. Each processing module 212–214 has a process chamber entrance 216 for providing access to the respective process module chamber. Likewise, inspection module 10 includes entrance 27 for providing access to the inspection module.

A common material transport arm 220 interfaces with substrate loading input 204, substrate unloading input 206, processing modules 212–214 and inspection module 10 along a predefined substrate travel path. In FIG. 6, transport arm 220 is shown transporting a substrate 222 into processing module 214. When substrate 222 is to be inspected, transport arm 220 transfers substrate 222 through entrance 27 and into the enclosure of inspection module 10.

As described above, inspection module computer controller 26 is coupled to inspection module 10 for controlling the inspection operation and for performing image analysis. Inspection module computer controller 26 is also coupled to a cluster tool computer 232, which controls cluster tool system 200 and its transport arm 220. Inspection module computer controller 26 communicates with cluster tool computer 232 for scheduling the inspection step in the overall process sequence determined by computer 232. In some embodiments of the present invention, transport arm 220 is controlled by its own computer controller 234. Inspection module computer controller 26 is coupled to transport arm computer controller 234 for communicating with transport arm computer controller 234.

In one embodiment, cluster tool system 200 is a substrate polishing and inspection cluster tool system in which substrate processing module 212 includes a substrate polishing or planarizing module, substrate processing module 213 includes a scrubbing module and substrate processing module 214 includes a rinsing module. An additional substrate processing module (not shown in FIG. 6) can also be added for drying the substrate after scrubbing and rinsing and before inspection.

Figure 7:
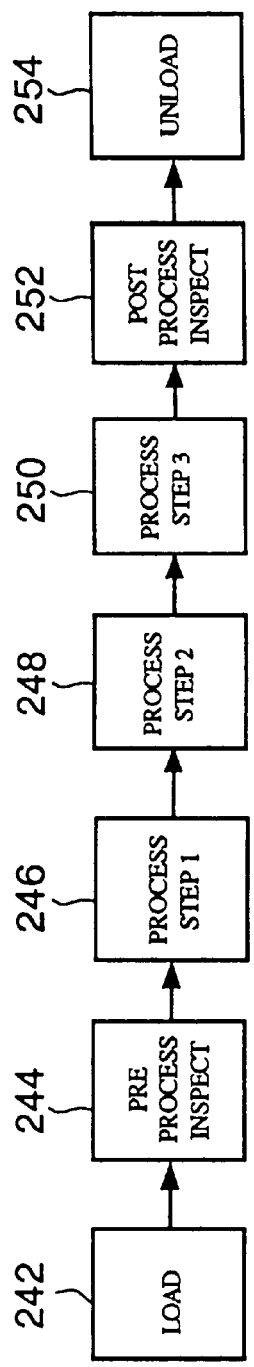
FIG. 7 is a flow chart showing a typical process sequence for the cluster tool system.

FIG. 7 is a flow chart showing a typical process sequence for substrate 222 in cluster tool system 200. At step 242, transport arm 220 loads substrate 222 from substrate loading input 204. At step 244, transport arm 220 transfers substrate 222 to inspection module 10 for a pre-process inspection. Once the pre-process inspection is complete, transport arm 220 transfers substrate 222 from inspection module 210 to processing modules 212–214, at steps 246–250. At step 252, transport arm 220 transfers substrate 222 from processing module 214 to inspection module 10 for a post-process inspection. Finally, transport arm 220 transfers substrate 222 to substrate unloading output 206, at step 254.

Figure 8:
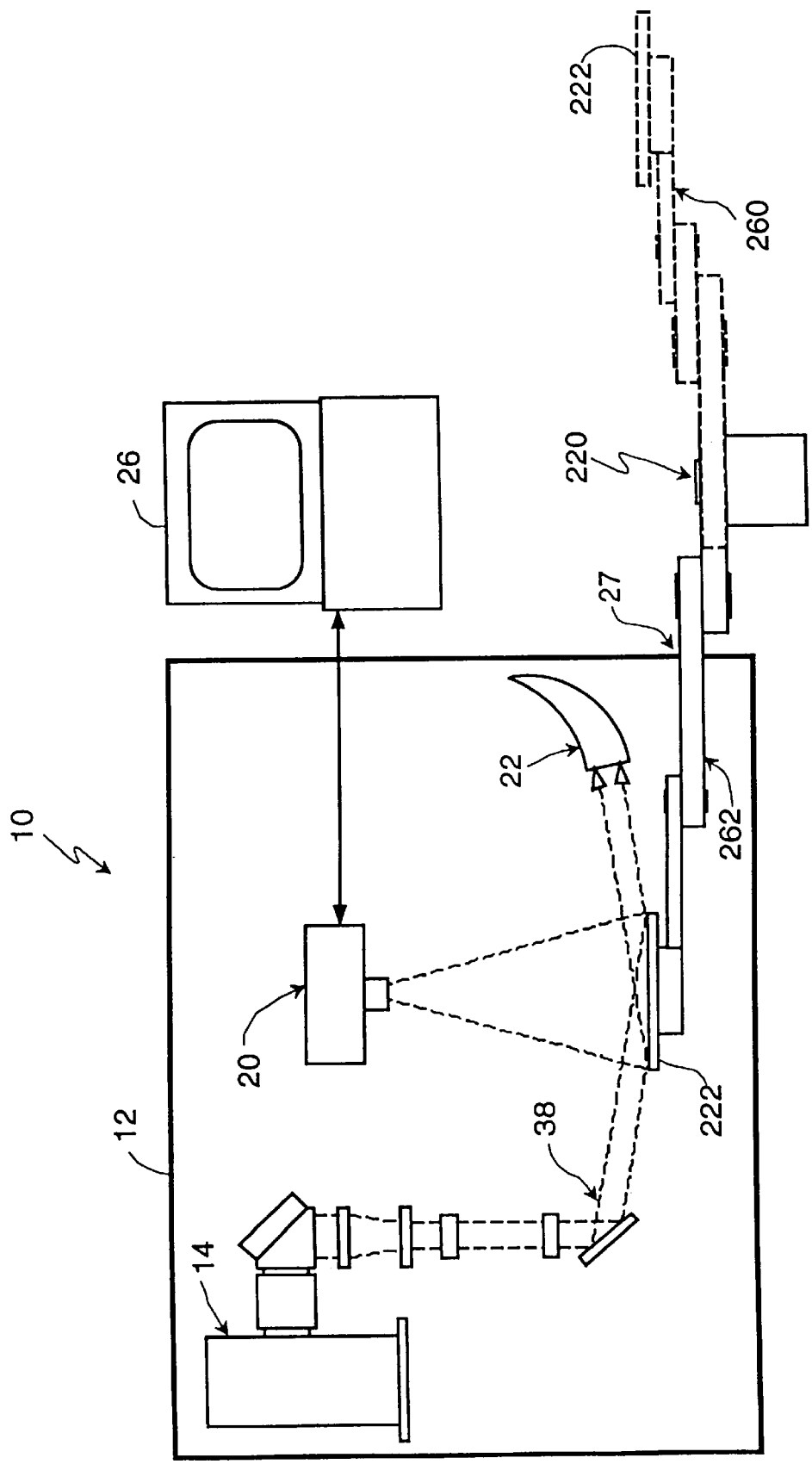
FIG. 8 is a schematic illustration showing insertion of a cluster tool transport arm into the inspection module.

FIG. 8 is a schematic illustration of inspection module 10, which shows the insertion of substrate 222 by transport arm 220 in greater detail. The same reference numerals are used in FIG. 8 as were used in FIGS. 1 and 6 for the same or similar elements. Transport arm 220 has a retracted position 260 (shown in phantom) relative to inspection module 10 in which substrate 222 is positioned external to enclosure 12. Transport arm 220 has an extended position 262 in which substrate 222 is positioned internal to enclosure 12. In extended position 262, transport arm 220 extends through entrance 27. Transport arm 220 preferably supports substrate 222 at a predetermined substrate holding position relative to light beam path 38 and camera 20 during the inspection process. A separate holder, such as holder 18 shown in FIG. 1, is not required. This eliminates contamination of the backside of substrate 222 caused by contact between the substrate and an additional holder. Another significant advantage of the embodiment shown in FIG. 8 is that there are no mechanically moving elements within enclosure 12, other than transport arm 220. This reduces the chance for contaminating the active surface of substrate 222 since there is no mechanical wear in the system for generating particles that might land on the substrate. Eliminating all moving parts also makes inspection module 10 highly reliable, which is an essential feature for semiconductor manufacturing equipment. With no moving parts, inspection module 10 is simpler and cheaper than inspection systems that require motion, such as translational or rotational movement of the substrate or light source to allow inspection of the entire substrate.

Figure 9:
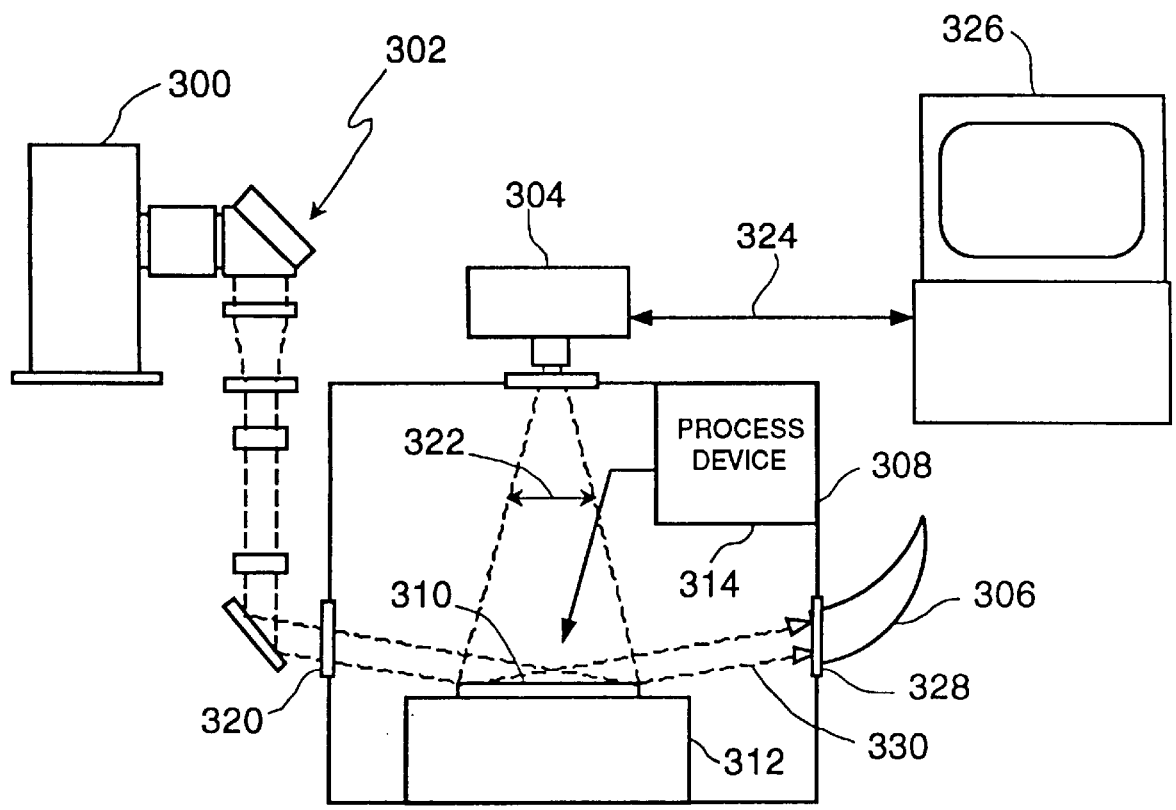
FIG. 9 is a diagram illustrating in-situ inspection within a substrate process module.

In another embodiment, the inspection module of the present invention is configured to perform in-situ inspection of particles on a substrate within a substrate processing chamber. FIG. 9 is a diagram illustrating in-situ inspection. Inspection module 299 includes light source 300, beam shaping and guiding optics 302, camera 304, light trap 306 and computer controller 326. These elements are substantially the same as those shown in FIG. 1. However, in the embodiment shown in FIG. 9, these elements are disposed around the exterior of a semiconductor processing chamber 308.

A substrate 310 is supported on a holder 312 within chamber 308. A substrate processing device 314 is supported within chamber 308 relative to substrate holder 312 for performing a manufacturing process step on substrate 310. Substrate processing device 314 can include a deposition or etching device which is operated under a vacuum, for example. In one embodiment of the present invention, chamber 308 is a load-lock chamber within which the atmosphere in the chamber is pumped down to a vacuum before the substrate is transferred into a subsequent vacuum process chamber. Chamber 308 includes an optically transparent window 320. Light source 300 and optics 302 are supported relative to window 320 such that the light source illuminates substantially the entire active surface of substrate 310 through window 320 at a grazing angle of incidence with respect to the active surface. Camera 304 is supported on the upper surface of chamber 308 and has a field of view 322, through another optically-transparent window 321, which covers substantially the entire active surface of substrate 310. Camera 304 is oriented to detect a fraction of the non-specularly reflected light that is scattered from any particles or other defects on the active surface. Once camera 304 acquires an image of substrate 310, camera 304 generates a digital output 324 representative of the intensity of the detected non-specularly reflected light per unit area of the active surface. Computer controller 326 is coupled to output 324 and performs the particle detection and analysis functions discussed above.

A second optically transparent window 328 is positioned within the walls of chamber 308 for transmitting specularly reflected light 330 to light trap 306. The embodiment shown in FIG. 9 can be used in a cluster tool system when a separate inspection station is not available to house the inspection module. The embodiment shown in FIG. 9 can also be used to retrofit existing process tools with in-situ particle detection capability.

The inspection module of the present invention is particularly well suited for use in substrate polishing processes, such as a chemical mechanical polishing "CMP" processes. In a CMP process, substrates are globally planarized. Substrates undergoing global planarization can include semiconductor wafers, multi-chip module electronic packaging substrates, rigid disk drive media, flat panel displays, and micro-electromechanical sensor substrates, for example.

Substrate polishing is a "dirty" operation, since a particle-based slurry is used as the polishing compound. Therefore, substrates are normally cleaned after the polishing operation, and there is a strong need for inspection of the substrates after cleaning to ensure the effectiveness of the cleaning process. The polishing operation results in a relatively smooth planarized surface that is especially amenable to a post-process grazing angle inspection step according to the present invention. With a patterned semiconductor wafer, light scattering from the pattern on the substrate surface, if present, is minimized. Therefore, there is no need for complex and time consuming inspection processes and analysis techniques for filtering images of patterned substrates.

Figure 11:
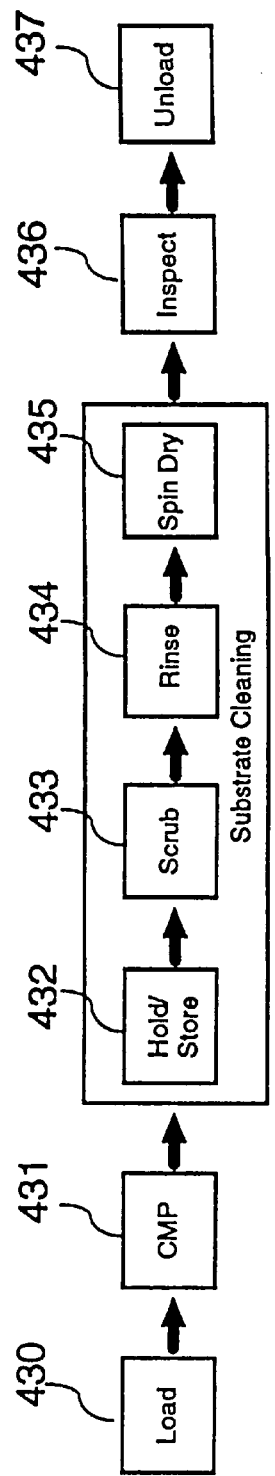
FIG. 11 is flow chart showing the process steps performed in the apparatus shown in FIG. 10.
Figure 10:
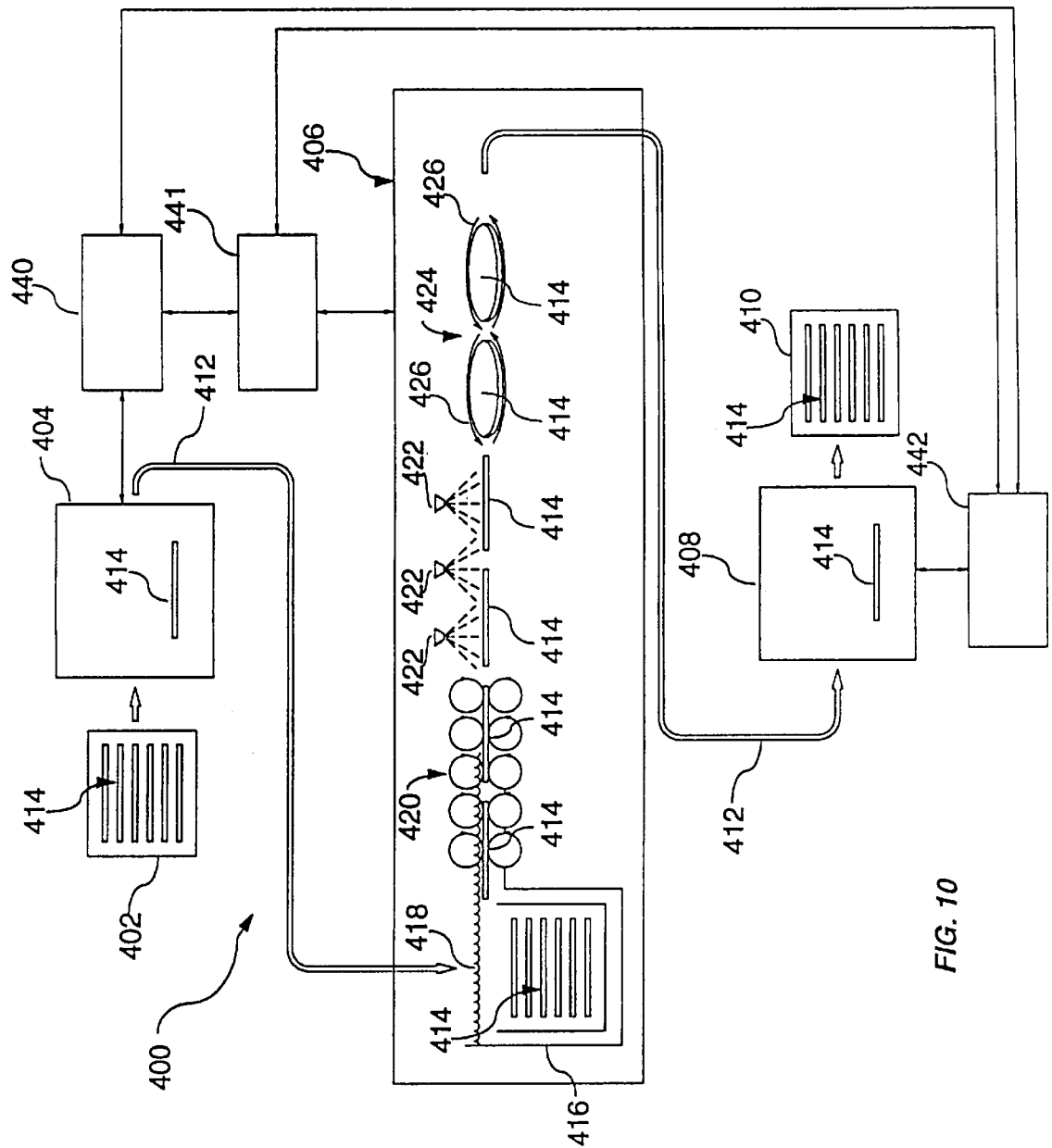
FIG. 10 is a schematic illustration of a substrate polishing and inspection apparatus according to one embodiment of the present invention.

FIG. 10 is a schematic illustration of a substrate polishing and inspection apparatus 400, which can be configured as an integrated cluster tool system or as separate, self-contained units according various embodiments of the present invention. FIG. 11 is flow chart showing the process steps performed in the apparatus shown in FIG. 10. Apparatus 400 includes a substrate loading carrier 402, a substrate polishing station 404, a substrate cleaning station 406, a substrate inspection station 408 and a substrate unloading carrier 410 which are positioned along a substrate travel path 412. Substrate loading carrier 402 holds a plurality of substrates 414 to be polished. Substrates 414 can be transported from station to station by a common material transport arm similar to that shown in FIG. 6.

At step 430, one or more of the substrates 414 are loaded from carrier 402 and placed into substrate polishing station (or cluster tool module) 404 where the substrates are planarized, at step 431. Substrate polishing station 404 has a computer-based controller 440 which controls the loading and unloading of substrates into station 404, the sequence of polishing steps within station 404. Controller 440 can also serve as a master controller for controlling the overall process sequence through apparatus 400, controlling the common substrate transport arm, if present, monitoring the status of each processing and inspection station and providing a user interface.

After polishing, substrates 414 are unloaded from substrate polishing station 404 and placed in a substrate holding tank 416 within cleaning station 406, at step 432. Holding tank 416 is filled with water 418, which covers substrates 414. This prevents the polishing compound used in polishing station 404 from drying on each substrate 414 before the substrate is cleaned. At step 433, substrates 414 are wet-cleaned on both surfaces, preferably using a rotating brush scrubber 420 in conjugation with a suitable surfactant. Next, at step 434, substrates 414 are rinsed, preferably with clean, filtered, deionized water, by sprayers 422. At step 435, substrates 414 are dried at drying station 424. Substrates 414 are preferably dried by spinning the substrates, as indicated by arrows 426. Cleaning station 406 can include one or more controllers 441 for controlling the various cleaning steps within station 406 and for communicating with controller 440. For example, controller 441 can communicate status information and scheduling information for the transport of substrates into and out of each cleaning step.

Once substrates 414 have been cleaned, the substrates are unloaded from substrate cleaning station 406 and loaded into substrate inspection station 408, at step 436, where each substrate is inspected for particles and other defects remaining on the substrate after polishing and cleaning. Substrate inspection station 408 preferably includes an inspection module similar to that shown in FIG. 1, wherein substantially the entire active surface of substrate 414 is illuminated with a light beam orientated at a grazing angle of incidence with respect to the active surface of the substrate. Any defects remaining on the active surface after polishing and cleaning scatter light from the light beam. The scattered light is applied to a photodetector array, such as photodetector array 62 shown in FIG. 1. Each pixel in the photodetector array corresponds to a unit area on active surface of the substrate. The plurality of pixels together have a field of view covering substantially the entire active surface. The intensity of the scattered light applied to the photodetector array is then measured. Computer controller 442, similar to controller 26 shown in FIG. 1, performs the detection and analysis procedures discussed above. After inspection, each substrate 414 is unloaded from substrate inspection station 408 and loaded into substrate unloading carrier 410, at step 437.

Controller 442 is coupled to controllers 440 and 441 for communicating status information and for scheduling the transport of substrates into and out of inspection module 408. In one embodiment, controller 442 communicates results of each inspection to master controller 440 and to controller 441. Based on the results of the inspection, master controller 440 can provide the appropriate data to its user interface or schedule additional process steps on selected substrates, if required. For example, if a particular substrate fails a specified inspection test, such as a maximum surface roughness test or a defect test, master controller 440 receives an indication of the failure from controller 442 and schedules an additional pass through polishing station 404, cleaning stations 406 or inspection station 408 for that substrate. Communications between each of the controllers are provided through standard SECS communications interfaces, for example.

Conclusion

The substrate inspection module of the present invention has a relatively low complexity and provides optimum sensitivity while minimizing inspection cycle time by imaging the entire substrate at one time. The inspection module has a substrate inspection cycle time of less than ten seconds, as compared to several tens of seconds for conventional substrate inspection methods. This makes it possible to inspect a substrate while the substrate sits on a common material transport arm without significantly reducing the amount of time that the arm is available for other tasks. This also makes it possible to integrate the inspection module in a multi-step process without significantly affecting the overall throughput of the process. The module itself has no moving parts. This reduces particle generation and further reduces inspection cycle time. The inspection module is also capable of providing in-situ detection of particles on wafers within a substrate processing chamber, including processing chambers operating under a vacuum. Another advantage of the inspection module of the present invention is that it is particularly well-suited for detecting particles on substrates subsequent to polishing and cleaning operations.

Although the present invention has been described with reference to preferred embodiments, workers skilled in the art will recognize that changes may be made in form and detail without departing from the spirit and scope of the invention.

What is claimed is:

1. An optical inspection cluster tool module for detecting particles on an active surface of a substrate in a cluster tool system, the optical inspection cluster tool module comprising:

an enclosure having a material transport aperture which is adapted to receive a common material transport arm;

a substrate holding position within the enclosure;

a light source having a light beam port;

a light beam path extending from the light beam port to the substrate holding position and having a grazing angle of incidence with respect to the active surface of the substrate, wherein the light beam path illuminates substantially the entire active surface;

a lens which is oriented to collect non-specularly reflected light that is scattered from the light beam path by any defects on the active surface, the lens having a focal plane; and a photodetector array having a plurality of pixels which are positioned within the focal plane of the lens, wherein each pixel corresponds to an area on the active surface and the plurality of pixels together form a field of view that covers substantially the entire active surface.

2. The optical inspection cluster tool module of claim 1 and further comprising a substrate holder secured within the enclosure at the substrate holding position.

3. The optical inspection cluster tool module of claim 1 wherein the optical inspection cluster tool module is free of mechanically-moving components within the enclosure.

4. The optical inspection cluster tool module of claim 1 wherein the light beam port comprises a broadband collimated, circular light beam port and the light beam path comprises a circular-to-rectangular beam shape converter.

5. The optical inspection cluster tool module of claim 1 wherein the light source comprises a monochromatic laser light source.

6. The optical inspection cluster tool module of claim 1 wherein the lens and the photodetector array together comprise a charge coupled device ("CCD") array camera.

7. The optical inspection cluster tool module of claim 6 wherein CCD array camera comprises a slow-scan, cooled CCD array camera.

8. The optical inspection cluster tool module of claim 1 wherein the lens and the photodetector array together comprise a video camera.

9. The optical inspection cluster tool module of claim 1 wherein the enclosure is light-proof.

10. The optical inspection cluster tool module of claim 1 wherein the enclosure comprises a light-absorbing internal surface.

11. The optical inspection cluster tool module of claim 1 and further comprising a beam trapping device which is oriented relative to the light beam path and the substrate holding position for trapping specularly reflected light from the active surface.

12. The optical inspection cluster tool module of claim 1 and further comprising means coupled to the photodetector array for measuring an intensity of the collected non-specular light within the focal plane at each of the plurality of pixels and for identifying presence of the defects as a function of the measured intensity.

13. The optical inspection cluster tool module of claim 1 and further comprising means coupled to the photodetector array for measuring an intensity of the collected non-specularly reflected light within the focal plane within at least one of the plurality of pixels and for measuring surface roughness based on the measured intensity.

14. The optical inspection cluster tool module of claim 1 and further comprising a light intensity controller coupled to the light source.

15. The optical inspection cluster tool module of claim 1 wherein the photodetector array has an output indicating light intensity applied within each of the plurality of pixels and wherein the module further comprises a computer controller coupled to the output.

16. The optical inspection cluster tool module of claim 1 wherein the enclosure comprises a vacuum chamber.

17. An integrated cluster tool system for processing a substrate having an active surface, the system comprising:
  a loading module having a substrate loading input;
  a plurality of substrate processing modules;
  a substrate inspection module comprising:
    an enclosure having a substrate loading aperture;
    a substrate holding position within the enclosure;
    a light source having a light beam port;
    a light beam path extending from the light beam port to the substrate holding position and having a grazing angle of incidence with respect to the active surface when the substrate is held in the substrate holding position, wherein the light beam path illuminates substantially the entire active surface;
    a lens which is oriented relative to the substrate holding position to collect non-specular light scattered from the light beam path by any defects, including particles, on the active surface, the lens having a focal plane; and
    a photodetector array having a plurality of pixels which are positioned within the focal plane of the lens, wherein each pixel corresponds to a unit area on the active surface and the plurality of pixels together have a field of view that covers substantially the entire active surface; and
  a common substrate transport arm which interfaces with the substrate loading input, each of the substrate processing modules and the substrate inspection module along a substrate travel path.

18. The integrated cluster tool system of claim 17 wherein the plurality of substrate processing modules comprises a substrate scrubbing module, a substrate rinsing module and a substrate drying module.

19. The integrated cluster tool system of claim 17 wherein the plurality of substrate processing modules further comprises a substrate polishing module.

20. The integrated cluster tool system of claim 17 wherein the substrate inspection module is free of mechanically-moving components within the enclosure.

21. The integrated cluster tool system of claim 17 wherein the common substrate transport arm comprises a substrate holder having a retracted position and an extended position, wherein the substrate holder is external to the enclosure when the common substrate transport arm is in the retracted position and wherein the substrate holder is internal to the enclosure and in the substrate holding position when the common substrate transport arm is in the extended position.

22. The integrated cluster tool system of claim 21 and further comprising:
  inspection controller means coupled to the light source, the photodetector array and the common substrate transport arm for controlling the light source to illuminate the active surface through the light beam path and for measuring a resulting intensity of the non-specularly scattered light within the plurality of pixels when the common substrate transport arm supports the substrate holder in the extended position.

23. The integrated cluster tool system of claim 17 and further comprising:
  cluster tool controller means operatively coupled to the loading module, the plurality of substrate processing modules, the substrate inspection module and the common substrate support arm for controlling a sequence of process steps on the substrate within the integrate cluster tool system; and
  wherein the substrate inspection module further comprises inspection controller means coupled to the light source, the photodetector array and the cluster tool controller means for controlling the light source to illuminate the active surface through the light beam path, measuring a resulting intensity of the non-specularly scattered light within the plurality of pixels, and providing an output indicative of the measured intensity to the cluster tool controller means.

24. An electronic substrate processing and inspection chamber for processing and in-situ inspecting an active surface of a electronic substrate, the chamber comprising:
  a chamber enclosure;
  an electronic substrate holder positioned within the chamber enclosure for holding the electronic substrate;
  an electronic substrate processing device supported within the chamber enclosure relative to the electronic substrate holder;
  an optically transparent window formed in the chamber enclosure;
  illumination means supported external to the chamber enclosure for illuminating substantially the entire active surface of the electronic substrate through the optically transparent window at a grazing angle of incidence with respect to the active surface; and
  camera means having a field of view covering substantially the entire active surface of the electronic substrate for detecting non-specularly reflected light that is scattered from any defects on the active surface and for generating a digital output representative of intensity of the detected non-specularly reflected light per unit area of the active surface.

25. The electronic substrate processing and inspection chamber of claim 24 and further comprising means for digitally processing the digital output for detecting presence of the defects.

26. A method of processing and inspecting an active surface of a substrate, the method comprising:
  polishing the active surface;
  cleaning the active surface after polishing;
  illuminating substantially the entire active surface with a first light beam oriented at a grazing angle of incidence with respect to the active surface such that any defects remaining on the active surface after polishing and cleaning scatter light from the first light beam;
  applying the scattered light from the first light beam to a photodetector array having a plurality of pixels, wherein each pixel corresponds to a unit area on the active surface and the plurality of pixels together have a field of view covering substantially the entire active surface; and measuring intensity of the scattered light applied to the photodetector array.

27. The method of claim 26 and further comprising:

identifying any defects remaining on the active surface within each unit area as a function of the measured intensity within the corresponding pixel in the photodetector array.

28. The method of claim 27 wherein identifying any defects comprises:

comparing the measured intensity within each of the plurality of pixels with an intensity threshold;

identifying the pixels in which the measured intensity exceeds the intensity threshold;

identifying the unit areas on the active surface that correspond to the pixels in which the measured intensity exceeds the intensity threshold; and generating a list of defect locations based on the identified unit areas.

29. The method of claim 26 wherein the substrate comprises a patterned semiconductor wafer and wherein the method further comprises identifying defects on the active surface of the patterned semiconductor wafer as a function of the measured intensity within the plurality of pixels in the photodetector array.

30. The method of claim 26 wherein the defects include particles residing on the active surface following polishing and cleaning and wherein the method further comprises:

comparing the measured intensity within each of the plurality of pixels with an intensity threshold;

counting the pixels in which the measured intensity exceeds the intensity threshold;

generating a count of the particles residing on the active surface based on the count of pixels in which the measured intensity exceeds the threshold.

31. The method of claim 26 and further comprising:

comparing the measured intensity within each of the plurality of pixels with an intensity threshold;

identifying a group of the pixels in which the measured intensity exceeds the intensity threshold and in which each of the pixels in the group is spatially contiguous with the other pixels in the group within the photodetector array; and associating the group of the pixels with a single defect on the active surface.

32. The method of claim 26 and further comprising:

identifying scratches on the active surface produced by the step of polishing based on a pattern of the measured intensity within the plurality of pixels in the photodetector array.

33. The method of claim 26 wherein the active surface has a surface roughness following polishing and cleaning which scatters light from the first light beam and wherein the method further comprises:

measuring the surface roughness as a function of the measured intensity.

34. The method of claim 26 wherein the active surface has a surface roughness following polishing and cleaning which scatters light from the first light beam and wherein measuring intensity comprises:

measuring intensity within each of the plurality of pixels; and subtracting a surface roughness intensity value, which is representative of the surface roughness, from the measured intensity within each of the plurality of pixels.

35. The method of claim 26 wherein the substrate has a perimeter with an orienting feature and wherein the method further comprises:

illuminating the entire active surface and the entire perimeter of the substrate with a second light beam oriented at a substantially normal angle of incidence with respect to the active surface;

applying reflected light of the second light beam from the active surface to the photodetector array such that the plurality of pixels together have a second field of view which includes substantially the entire active surface and the entire perimeter; and measuring intensity of the applied reflected light;

identifying a position of the perimeter and a position of the orienting feature within the second field of view; and defining coordinates on the active surface based on the positions of the perimeter and the locating feature.

36. The method of claim 26 wherein polishing comprises planarizing the active surface with a chemical mechanical polisher.

37. The method of claim 26 wherein cleaning comprises mechanically scrubbing the active surface, rinsing the active surface with a liquid and spinning the active surface until the active surface is dry.

38. The method of claim 26 and further comprising:

transporting the substrate along a mechanical substrate transport path from a first substrate holder to a polishing station;

performing the step of polishing at the polishing station;

transporting the substrate along the mechanical substrate transport path from the polishing station to a cleaning station;

performing the step of cleaning at the cleaning station;

transporting the substrate along the mechanical substrate transport path from the cleaning station to an inspection station;

performing the steps collecting, transmitting, mapping and measuring at the inspection station; and transporting the substrate along the mechanical substrate transport path from the inspection station to a second substrate holder.

39. A substrate polishing and inspection apparatus comprising:

a substrate travel path for carrying a substrate having an active surface to be polished;

a polishing station positioned along the substrate travel path;

a cleaning station positioned along the substrate travel path, downstream of the polishing station;

a drying station positioned along the substrate travel path, downstream of the cleaning station; and a substrate inspection station positioned along the substrate travel path, downstream of the drying station and comprising:

an enclosure having a substrate loading aperture which communicates with the substrate travel path;

a substrate holding position within the enclosure;

a light source having a light beam port;

a light beam path extending from the light beam port to the substrate holding position and having a grazing angle of incidence with respect to the active surface when the substrate is held in the substrate holding position, wherein the light beam path illuminates substantially the entire active surface;

a lens which is oriented relative to the substrate holding position to collect non-specularly reflected light scattered from the light beam path by any defects, including particles, on the active surface, the lens having a focal plane; and a photodetector array having a plurality of pixels which are positioned within the focal plane of the lens, wherein each pixel corresponds to a unit area on the active surface and the plurality of pixels together have a field of view that covers substantially the entire active surface.

40. The apparatus of claim 38 and further comprising:

first controller means operatively coupled to the polishing station, the cleaning station, the drying station and the inspection station for controlling a sequence of process steps on the substrate within the apparatus; and wherein the substrate inspection station further comprises second controller means coupled to the light source, the photodetector array and the first controller means for controlling the light source to illuminate the active surface through the light beam path, measuring a resulting intensity of the non-specularly scattered light within the plurality of pixels, and providing an output indicative of the measured intensity to the first controller means.

* * * * *